United States Patent
Bian et al.

(10) Patent No.: US 11,014,129 B2
(45) Date of Patent: May 25, 2021

(54) METHODS OF CLEANING A PROTEIN A BASED AFFINITY CHROMATOGRAPHY COLUMN

(71) Applicant: EMD Millipore Corporation, Burlington, MA (US)

(72) Inventors: Nanying Bian, Lexington, MA (US); Sapna Mehtani, Somerville, MA (US); John Dana Hubbard, Billerica, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 14/912,440

(22) PCT Filed: Jun. 19, 2014

(86) PCT No.: PCT/US2014/043095
§ 371 (c)(1),
(2) Date: Feb. 17, 2016

(87) PCT Pub. No.: WO2015/034566
PCT Pub. Date: Mar. 12, 2015

(65) Prior Publication Data
US 2016/0193633 A1    Jul. 7, 2016

Related U.S. Application Data

(60) Provisional application No. 61/873,450, filed on Sep. 4, 2013.

(51) Int. Cl.
*B08B 9/027*    (2006.01)
*C07K 1/22*    (2006.01)
(Continued)

(52) U.S. Cl.
CPC .......... *B08B 9/027* (2013.01); *A61L 2/18* (2013.01); *B08B 3/08* (2013.01); *C07K 1/22* (2013.01)

(58) Field of Classification Search
CPC .. B01D 15/20; B01D 15/203; B01D 15/3804; B01D 15/3809; B01J 20/28;
(Continued)

(56) References Cited

U.S. PATENT DOCUMENTS 7,846,336 B2 * 12/2010 Burg ............... B01J 49/53
210/656
7,951,885 B2    5/2011 Joehnok et al.
(Continued)

FOREIGN PATENT DOCUMENTS

CN    101302504 A    11/2008
CN    102895960 A    1/2013
(Continued)

OTHER PUBLICATIONS

International Search Report Received for PCT Application No. PCT/US2014/043095, dated Oct. 1, 2014, 4 pages.
(Continued)

*Primary Examiner* — Nadine G Norton
*Assistant Examiner* — Christopher Remavege
(74) *Attorney, Agent, or Firm* — EMD Millipore Corporation

(57) ABSTRACT

The present invention provides methods for cleaning a Protein A chromatography column employing a media comprising a Protein A ligand derived from the C domain of *Staphylococcus aureus*, such that the column can be cleaned using both acidic and alkaline solutions.

20 Claims, 2 Drawing Sheets
Specification includes a Sequence Listing.

(51) Int. Cl.
*A61L 2/18* (2006.01)
*B08B 3/08* (2006.01)

(58) Field of Classification Search
CPC ...... B01J 20/285; B01J 20/30; B01J 20/3085; B01J 20/34; B01J 20/345; B01J 20/3425; B01J 20/3475; B01J 20/3202; B01J 20/3206; B01J 20/3208; B01J 20/321; B01J 20/3212; G01N 30/50; G01N 30/48; G01N 30/482; G01N 30/528; G01N 30/52; C07K 1/16; C07K 1/22
USPC ..... 134/22.13, 22.17, 22.1, 22.11, 26, 22.12, 134/29, 28; 210/656, 660
See application file for complete search history.

(56) References Cited

U.S. PATENT DOCUMENTS

| | | | | |
|---|---|---|---|---|
| 8,674,073 | B2* | 3/2014 | Majima | B01J 20/286 530/350 |
| 9,102,709 | B1* | 8/2015 | Ladiwala | C07K 1/22 |
| 2005/0006307 | A1* | 1/2005 | Jones | A61L 2/18 210/636 |
| 2005/0038231 | A1* | 2/2005 | Fahrner | C07K 16/065 530/387.1 |
| 2005/0056592 | A1* | 3/2005 | Braunger | B01D 15/426 210/660 |
| 2008/0230478 | A1* | 9/2008 | Johansson | C07K 1/22 210/656 |
| 2010/0056645 | A1* | 3/2010 | Deorkar | A01N 31/02 514/730 |
| 2010/0112597 | A1* | 5/2010 | Bian | G01N 33/6854 435/7.1 |
| 2010/0221844 | A1* | 9/2010 | Bian | B01J 20/3244 436/501 |
| 2011/0190194 | A1* | 8/2011 | Lim | A61P 29/00 514/1.4 |
| 2012/0289680 | A1* | 11/2012 | Hall | C07K 14/31 530/324 |
| 2013/0046056 | A1 | 2/2013 | Spector et al. | |
| 2013/0165539 | A1* | 6/2013 | Carbonell | B01D 15/3804 521/31 |
| 2015/0093800 | A1* | 4/2015 | Mahajan | B01J 49/0078 435/188 |

FOREIGN PATENT DOCUMENTS

| | | |
|---|---|---|
| EP | 2527429 A2 | 11/2012 |
| EP | 2532672 A2 | 12/2012 |
| KR | 101880565 B1 | 7/2018 |
| WO | 00/23580 A1 | 4/2000 |
| WO | 2008/039141 A1 | 4/2008 |
| WO | 2010/066676 A1 | 6/2010 |
| WO | 2015/034566 A1 | 3/2015 |

OTHER PUBLICATIONS

Han et al., "Recovery and Purification of Antibody", Antibody Expression and Production, Cell Engineering, vol. 7, 2011, pp. 305-340.
Andersen et al., "CIP Technology: Challenges and Trends", Manufacturing, Innovations in Pharmaceutical Technology, Apr. 24, 2008, pp. 84-86.
GE Healthcare, Life Sciences, "MabSelect SuRe LX", available online at <http://www.gelifesciences.com/webapp/wcs/stores/servlet/productById/en/GELifeSciences-US/17547401>, Retrieved on Mar. 6, 2014, 1 page.
Grönberg et al., "A Tool for Increasing the Lifetime of Chromatography Resins", mAbs, vol. 3, No. 2, Mar./Apr. 2011, pp. 192-202.
Gueffroy, Donald E., "Buffers: A Guide for the Preparation and Use of Buffers in Biological Systems", Calbiochem-Behring Corporation, Copyright 1975, 24 pages.
Hagel et al., "Cleaning and Sanitization", Chapter 6, Handbook of Process Chromatography-Development, Manufacturing, Validation and Economics, Second Edition, 2008, pp. 147-159.
Hermanson et al., "Immobilized Affinity Ligand Techniques", Academic Press, Inc. San Diego, California, 1992, pp. 51-136.
Millipore Corporation, "Maintenance Guide for Tangential Flow Filters and Systems", 1989, pp. 1-23.
Pace et al., "How to Measure and Predict the Molar Absorption Coefficient of a Protein", Protein Science, Cambridge University Press, vol. 4, Issue 11, Nov. 1995, pp. 2411-2423.
Pall, Life Sciences, "Membrane Cassette Care and Use Procedures", User Guide, R00640 Rev B, 2006, pp. 1-45.
Rogers et al., "Development of a Rapid Sanitization Solution for Silica-Based Protein A Affinity Adsorbents", Journal of Chromatography A, vol. 1216, No. 21, May 2009, pp. 4589-4596.
Rosner, Dietmar, "The Composition of Cleaning Agents for the Pharmaceutical Industries", Chapter 4, Clean-in-Place for Biopharmaceutical Processes, First Edition, Oct. 15, 2007, pp. 53-72.
Sjödahl, Jörgen, "Structural Studies on the Four Repetitive Fc-Binding Regions in Protein A from *Staphylococcus aureus*", European Journal of Biochemistry, vol. 78, No. 2, Sep. 1977, pp. 471-490.
Turková, J., "Solid Matrix Supports", Bioaffinity Chromatography, Elsevier, B.V., 1993, pp. 171-214.
Uhlen et al., "Complete Sequence of the Staphylococcal Gene Encoding Protein A. A Gene Evolved through Multiple Duplications", The Journal of Biological Chemistry, vol. 259, No. 3, Feb. 10, 1984, pp. 1695-1702.

\* cited by examiner

SEQUENCE LISTING

```
<160> NUMBER OF SEQ ID NOS: 4

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

```
<210> SEQ ID NO 2
<211> LENGTH: 174
<212> TYPE: DNA
<213> ORGANISM: Staphylococcus aureus

<400> SEQUENCE: 2
gcggataaca aattcaacaa ggagcaacag aacgcattct atgaaattct gcacctgccg      60
aatctgacgg aggagcaacg taacggcttt atccagtccc tgaaggatga tccgtctgtg     120
tctaaagaga tcctggcgga ggcaaaaaaa ctgaatgatg cacaagctcc gaaa           174

<210> SEQ ID NO 3
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Lys Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu
65                  70                  75                  80

Thr Glu Glu Gln Arg Asn Lys Phe Ile Gln Ser Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys Ala Asp Asn Lys Phe Asn Lys Glu Gln Gln Asn Ala
        115                 120                 125

Phe Tyr Glu Ile Leu His Leu Pro Asn Leu Thr Glu Glu Gln Arg Asn
    130                 135                 140

Lys Phe Ile Gln Ser Leu Lys Asp Asp Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190

Leu Pro Asn Leu Thr Glu Glu Gln Arg Asn Lys Phe Ile Gln Ser Leu
        195                 200                 205

Lys Asp Asp Pro Ser Val Ser Lys Glu Ile Leu Ala Glu Ala Lys Lys
    210                 215                 220

Leu Asn Asp Ala Gln Ala Pro Lys Ala Asp Asn Lys Phe Asn Lys Glu
225                 230                 235                 240

Gln Gln Asn Ala Phe Tyr Glu Ile Leu His Leu Pro Asn Leu Thr Glu
                245                 250                 255

Glu Gln Arg Asn Lys Phe Ile Gln Ser Leu Lys Asp Asp Pro Ser Val
            260                 265                 270

Ser Lys Glu Ile Leu Ala Glu Ala Lys Lys Leu Asn Asp Ala Gln Ala
        275                 280                 285

Pro Lys

```
                                                        290

<210> SEQ ID NO 4
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Phe Asn Lys Glu Gln Gln Asn Ala Phe Tyr Glu Ile Leu His Leu
1               5                   10                  15

Pro Asn Leu Thr Glu Glu Gln Arg Asn Lys Phe Ile Gln Ser Leu Lys
            20                  25                  30

Asp Asp Pro Ser Val Ser Lys Glu Ile Leu Ala Glu Ala Lys Lys Leu
        35                  40                  45

Asn Asp Ala Gln Ala Pro Lys Phe Asn Lys Glu Gln Gln Asn Ala Phe
50                  55                  60

Tyr Glu Ile Leu His Leu Pro Asn Leu Thr Glu Glu Gln Arg Asn Lys
65                  70                  75                  80

Phe Ile Gln Ser Leu Lys Asp Asp Pro Ser Val Ser Lys Glu Ile Leu
                85                  90                  95

Ala Glu Ala Lys Lys Leu Asn Asp Ala Gln Ala Pro Lys Phe Asn Lys
            100                 105                 110

Glu Gln Gln Asn Ala Phe Tyr Glu Ile Leu His Leu Pro Asn Leu Thr
            115                 120                 125

Glu Glu Gln Arg Asn Lys Phe Ile Gln Ser Leu Lys Asp Asp Pro Ser
        130                 135                 140

Val Ser Lys Glu Ile Leu Ala Glu Ala Lys Lys Leu Asn Asp Ala Gln
145                 150                 155                 160

Ala Pro Lys Phe Asn Lys Glu Gln Gln Asn Ala Phe Tyr Glu Ile Leu
                165                 170                 175

His Leu Pro Asn Leu Thr Glu Glu Gln Arg Asn Lys Phe Ile Gln Ser
            180                 185                 190

Leu Lys Asp Asp Pro Ser Val Ser Lys Glu Ile Leu Ala Glu Ala Lys
        195                 200                 205

Lys Leu Asn Asp Ala Gln Ala Pro Lys Phe Asn Lys Glu Gln Gln Asn
    210                 215                 220

Ala Phe Tyr Glu Ile Leu His Leu Pro Asn Leu Thr Glu Glu Gln Arg
225                 230                 235                 240

Asn Lys Phe Ile Gln Ser Leu Lys Asp Asp Pro Ser Val Ser Lys Glu
                245                 250                 255

Ile Leu Ala Glu Ala Lys Lys Leu Asn Asp Ala Gln Ala Pro Lys
            260                 265                 270
```

METHODS OF CLEANING A PROTEIN A BASED AFFINITY CHROMATOGRAPHY COLUMN

CROSS-REFERENCE TO RELATED APPLICATIONS AND SEQUENCE LISTING

The present application is a U.S. National Stage Application of International Application No. PCT/US2014/043095, filing date Jun. 19, 2014, which claims the benefit of priority of U.S. Patent Application No. 61/873,450, filing date Sep. 4, 2013, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Dec. 14, 2015, is named P13-136US_SL.txt and is 6,325 bytes in size.

FIELD OF THE INVENTION

The present invention provides methods for cleaning a Protein A chromatography column. Moreover, it relates to methods for cleaning a Protein A based affinity chromatography column which employs an affinity chromatography media containing a ligand based on the C domain of *Staphylococcus aureus* Protein.

BACKGROUND OF THE INVENTION

The instant application contains a Sequence Listing which has been submitted electronically in ASCII format and is hereby incorporated by reference in its entirety. Said ASCII copy, created on Jun. 3, 2014, is named P13-136PCT_SL.txt and is 6,289 bytes in size.

Conventional processes for protein purification typically involve cell culture methods, e.g., using either mammalian or bacterial cell lines recombinantly engineered to produce the protein of interest followed by: (a) a clarification step for the removal of cells and cellular debris, e.g., using differential centrifugation and/or filtration; and (b) one or more downstream chromatography steps to separate the protein of interest from various impurities in the clarified cell culture feed.

In case of monoclonal antibodies and other Fc-containing proteins, the industry standard for purification typically involves a multi-step process. One of the important steps is a purification step which employs an affinity ligand called Protein A, which binds the Fc-region of antibodies. Typically, a large percentage of impurities are removed in this step. Although, Protein A affinity chromatography is a very effective step during the purification of antibodies, one disadvantage of using Protein A is that it is very expensive compared to ion exchange resins. Further packing and unpacking of the affinity chromatography columns is also very labor intensive and entails significant buffer cost. Therefore, it is desirable to be able to clean, re-use and sanitize the Protein A column for several cycles.

Currently, chromatography columns employing most commercially available Protein A media are cleaned using either alkaline conditions or acidic conditions. For example, chromatography columns employing MabSelect Sure® (GE), KanCap A (Kaneka) and ToyoPearl® AF-rProtein A 650F (Tosoh) media are cleaned using an alkaline solution, such as sodium hydroxide, whereas, chromatography columns employing ProSep® Ultra Plus media (EMD Millipore Corporation) use an acidic solution for cleaning.

SUMMARY OF THE INVENTION

The present invention provides methods for cleaning a chromatography column employing a media containing a ligand based on the C domain of *Staphylococcus aureus* Protein A immobilized onto a solid support, where the column can be cleaned using both acidic and alkaline solutions.

As discussed above, chromatography columns employing most commercially available Protein A media can be cleaned using either an acidic solution or an alkaline solution due to the instability of either the Protein A ligand or base matrix towards extended exposure to acidic or alkaline solution. A purification process employing such a chromatography column is set up accordingly, to either accommodate cleaning under alkaline conditions only or cleaning under acidic conditions only.

The methods according to the present invention enable a chromatography column employing a media comprising a ligand based on the C domain of Protein A immobilized onto a solid support, to be cleaned under acidic conditions, in addition to or as an alternative to cleaning under alkaline conditions, thereby providing greater flexibility in operation. By enabling efficient cleaning of the chromatography columns employing such a media, the methods described herein are able to preserve the binding capacity of the column over numerous cycles. Further, by enabling the cleaning of a chromatography column employing such a media, greater impurity removal is achieved compare to using either alkaline conditions or acidic conditions alone for cleaning, thereby resulting in greater product purity.

In some embodiments, a method of preserving the binding capacity of an affinity chromatography column over one or more affinity purification cycles is provided, the method comprising cleaning the chromatography column after one or more affinity purification cycles with an acidic solution having a pH lower than 3.0, wherein the affinity chromatography column comprises a media comprising a Protein A ligand derived from the C domain of *Staphylococcus aureus* Protein A immobilized onto a solid support comprising a polymer selected from the group consisting of polyvinylether, polyvinylalcohol, polymethacrylate, polyacrylate, polystyrene, polyacrylamide, polymethacrylamide and polycarbonate.

In some other embodiments, a method of cleaning an affinity chromatography column using both acidic and alkaline solutions is provided, where the method comprises: (a) contacting the column with both acidic and alkaline solutions after a cycle; or (b) contacting the column with either an acidic solution after a cycle or an alkaline solution after a cycle, such that the acidic and alkaline solutions are used in an alternating manner, wherein the affinity chromatography column comprises a media comprising a Protein A ligand derived from the C domain of *Staphylococcus aureus* Protein A immobilized onto a solid support.

In some embodiments, the Protein A ligand comprises an amino acid sequence selected from SEQ ID NO:3 and SEQ ID NO:4.

In some embodiments, the solid support comprises a polymer selected from the group consisting of polyvinylether, polyvinylalcohol, polymethacrylate, polyacrylate, polystyrene, polyacrylamide, polymethacrylamide and polycarbonate. In a particular embodiment, the solid support comprises a polyvinylether polymer.

In some embodiments, the acidic solution has a pH of 1.5 or a pH of 2.0 or a pH of 2.5.

In some embodiments, the binding capacity is preserved over 10 or more cycles. In other embodiments, the binding capacity is preserved over 50 or more cycles. In yet other embodiments, the binding capacity is preserved over 100 or more cycles. In still other embodiments, the binding capacity is preserved over 200 or more cycles.

Also provided herein is a method for sanitizing an affinity chromatography column after use while maintaining the binding capacity of the column, where the method comprises contacting the affinity chromatography column with a solution comprising phosphoric acid, acetic acid and benzyl alcohol for at least three hours, and wherein the affinity chromatography column comprises a Protein A ligand derived from the C domain of *Staphylococcus aureus* Protein A immobilized onto a solid support selected from the group consisting of polyvinylether, polyvinylalcohol, polymethacrylate, polyacrylate, polystyrene, polyacrylamide, polymethacrylamide and polycarbonate.

DETAILED DESCRIPTION OF THE INVENTION

Figure 1:
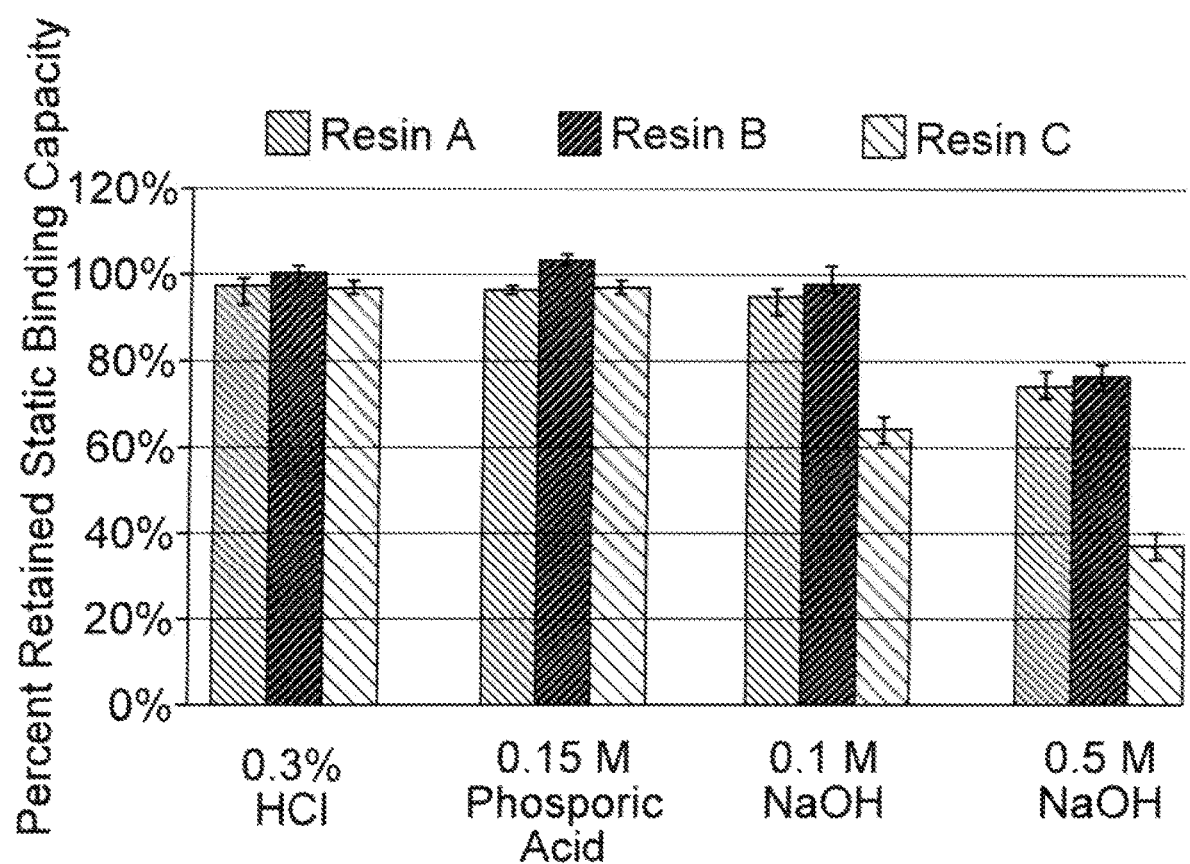
FIG. 1 is a bar graph depicting the results of an experiment to measure the percent retained static binding capacity of resins A. B and C upon exposure to: (1) 0.3% hydrochloric acid pH 1.5; (2) 0.15 M phosphoric acid, pH 1.5; (3) 0.1 M NaOH; and (4) 0.5 M NaOH, for 25 hrs, which is equivalent to 100 cycles (at 15 min/cycle). All three resin samples demonstrate retention of more than 95% binding capacity upon exposure to 0.3% HCl and 0.15 M $H_3PO_4$ after 25 hr exposure relative to the control. Resins A and B retain more than 95% binding capacity upon exposure to 0.1 M NaOH relative to the control. Resins A and B retain approximately 75% of binding capacity upon exposure to 0.5 M NaOH relative to the control. Resin C retains approximately 65% binding capacity upon exposure to 0.1 M NaOH relative to the control. Resin C retains approximately 38% of binding capacity upon exposure to 0.5 M NaOH relative to the control. Standard deviation is approximately 3%.

Protein A affinity chromatography involves binding of an Fc-containing protein (e.g., an immunoglobulin or another Fc-fusion protein) to a Protein A resin or media (i.e., a Protein A ligand immobilized onto a solid support) packed in the column and subsequent elution of the Fc-containing protein from the column. Cleaning-in-place (CIP) is crucial for efficient use of a chromatography column and to maximize the number of cycles that a column can be reused for. A cleaning procedure that efficiently removes impurities without being harmful to the chromatography resin is generally required. One of the most common cleaning solutions typically used for cleaning as well as sanitization of majority of the commercially available Protein A resins is sodium hydroxide (NaOH) (see, e.g., Hagel L et. al. Handbook of Process Chromatography—Development, Manufacturing, Validation and Economics. Second edition. London, UK: Academic Press; 2008. Cleaning and Sanitization; pp. 147-159; Gronberg et al., MAbs. 2011 March-April; 3(2): 192-202). Typically, when performing numerous subsequent cycles in column mode, there can be a gradual buildup of contaminants on the chromatography resin, causing fouling of the column and a reduced efficiency and binding capacity of the column. An efficient cleaning procedure between cycles minimizes the buildup of contaminants on the chromatography column, thereby extending the life of the column. This is also referred to as column regeneration.

While most commercially available Protein A resins are cleaned using an alkaline solution such as sodium hydroxide, the ProSep® Ultra Plus resin (EMD Millipore Corporation) is cleaned using phosphoric acid ($H_3PO_4$).

The present invention is based, at least on the surprising and unexpected discovery that, a chromatography column employing a media containing a ligand based on the C domain of *Staphylococcus aureus* Protein A immobilized onto a solid support can be cleaned with both acid and alkaline solutions. By enabling the cleaning of a column with both acidic and alkaline solutions, not only greater flexibility in operation is achieved but also when using both alkaline and acidic solutions for cleaning during a purification process, greater protein purity is achieved.

In order that the present disclosure may be more readily understood, certain terms are first defined. Additional definitions are set forth throughout the detailed description.

I. Definitions

As used herein, the term "SpA" "Protein A" or "*Staphylococcus aureus* Protein A." refers to a 42 kDa multi-domain protein isolated from the bacterium *Staphylococcus aureus*. SpA is bound to the bacterial cell wall via its carboxy-terminal cell wall binding region, referred to as the X domain. At the amino-terminal region, it includes five immunoglobulin-binding domains, referred to as E, D, A, B, and C (Sjodhal, Eur J Biochem. September 78(2):471-90 (1977); Uhlen et al., J Biol Chem. February 259(3):1695-702 (1984)). Each of these domains contains approximately 58 amino acid residues, and they share 65-90% amino acid sequence identity.

Each of the E, D, A, B and C domains of SpA possess distinct Ig-binding sites. One site is for Fc (the constant region of IgG class of g) and the other is for the Fab portion of certain Ig molecules (the portion of the Ig that is responsible for antigen recognition). It has been reported that each of the domains contains a Fab binding site. The non-Ig binding portion of SpA is located at the C-terminus and is designated the X region or X-domain.

As used interchangeably herein, the terms "C domain," "C domain of SpA," "C domain of Protein A" and "C domain of *Staphylococcus aureus* Protein A," refer to the polypeptide whose amino acid sequence is set forth in SEQ ID NO:1 or that encoded by, e.g., the nucleotide sequence set forth in SEQ ID NO:2. The "C domain" is a 58 amino acid polypeptide that folds into a three-helix bundle structure. It is capable of Fc binding via residues on the surface of helices 1 and 2, or to Fab via residues on the surface of helices 2 and 3.

Protein A ligands based on the C domain of Protein A, as used in the methods described herein, include ligands having an amino acid sequence at least 80%, or at least 85%, or at least 90%, or at least 95%, or more identical to the amino acid sequence set forth in SEQ ID NO: 1.

In various embodiments, a Protein A ligand based on the C domain of Protein A used in the methods described herein comprises the amino acid sequence set forth in SEQ ID NO:3 or SEQ ID NO:4.

The term "chromatography," as used herein, refers to a dynamic separation technique which separates a target molecule such as a target protein (e.g., an immunoglobulin or another Fc-containing protein) from other molecules in the mixture and allows it to be isolated. Typically, in a chromatography method, a mobile phase (liquid or gas) transports a sample containing the target molecule of interest across or through a stationary phase (normally solid) medium. Differences in partition or affinity to the stationary phase causes the temporary binding of selected molecules to the stationary phase while the mobile phase carries different molecules out at different times.

The term "affinity chromatography," as used herein, refers to a mode of chromatography where a target molecule, such as a protein molecule (e.g., an Fc-containing protein) to be separated is isolated by its lock-and-key interaction with a molecule (e.g., a Protein A based ligand) immobilized on the chromatography resin. This specific interaction allows the target molecule to bind while the undesirable molecules to flow through. Changing in temperature, pH, ionic strength of the mobile phase then releases the target molecule in high purity. In various embodiments described herein, affinity chromatography involves the addition of a sample containing a target molecule (e.g., an immunoglobulin or another Fc-containing protein) to a solid support which carries on it a ligand based on the C domain of Protein A (referred to as Protein A affinity chromatography media or resin).

The term "Protein A affinity chromatography," as used herein, refers to the separation or isolation of substances using Protein A or SpA-based ligands based on the C domain of Protein A, such as those described herein, where the SpA or Protein A ligand is immobilized on a solid support.

The term "ligand." as used herein, refers to a biological molecule based on the C domain of Protein A which is immobilized on a solid support (e.g., a porous surface) and which is capable of binding an Fc-containing protein. In some embodiments described herein, the ligand comprises the amino acid sequence set forth in SEQ ID NO:3, or variants, fragments or derivatives thereof. In some other embodiments described herein, the ligand comprises the amino acid sequence set forth in SEQ ID NO:4, or variants, fragments or derivatives thereof.

The term "solid support" refers in general to any material (porous or non porous) to which a ligand is attached. The attachment of ligands to the solid support can either be through a covalent bond, such as in the case of grafting (via ether, thioether, carbon-carbon bond, or other linkages), or through coating, adhesion, adsorption, and similar mechanisms. Exemplary solid supports used in the methods described herein include polyvinylether, polyvinylalcohol, polymethacrylate, polyacrylate, polystyrene, polyacrylamide, polymethacrylamide and polycarbonate.

Examples of Protein A affinity chromatography media/resin known in the art include those having the Protein A immobilized onto a controlled pore glass backbone, e.g., PROSEP® A and PROSEP® vA media/resin (EMD MILLIPORE); those having Protein A immobilized onto a polystyrene solid phase, e.g., the POROS® 50A and POROS® MabCapture™ A media/resin (APPLIED BIOSYSTEMS. INC.); and those having Protein A immobilized on an agarose solid support, e.g., rPROTEIN A SEPHAROSE FAST FLOW™ or MABSELECT™ media or resins (GE HEALTHCARE). In various embodiments, the Protein A ligands employed in the methods described herein are immobilized onto a solid support selected from the group consisting of polyvinylether, polyvinylalcohol, polymethacrylate, polyacrylate, polystyrene, polyacrylamide, polymethacrylamide and polycarbonate.

In a particular embodiment, the ligands used in the methods described herein are immobilized onto a polyvinylether polymer. See, e.g., U.S. Pat. No. 7,951,885, incorporated by reference herein in its entirety.

The term "affinity resin" or "affinity chromatography resin" or "affinity media" or "affinity chromatography media, as used interchangeably herein, refers to an affinity chromatography ligand (e.g., based on the C domain of Protein A) attached to a solid support such as, e.g., those described herein. In general, the terms "resin" and "media" are used interchangeably herein.

The term "target protein" or "protein of interest." as used interchangeably herein, refers to any protein that can be purified using the C domain of Protein A, or a variant or derivative thereof. In various embodiments, the target protein is an Fc-containing protein such as, e.g. an immunoglobulin or an Fc-fusion protein.

The term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions". "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions". "light chain variable domains". "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example. IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')$_2$, Fc and/or Fv fragments.

Methods of the invention can be used during the purification of any antibody or fragment thereof which can bind to Protein A, including but not limited to, human antibodies, humanized antibodies, chimeric antibodies, or fragments thereof. In some embodiments, the methods described herein are used during the purification of therapeutic antibodies.

Exemplary therapeutic antibodies include Herceptin™; Rituxan™; Avastin™; Bexxar™; Campath™; Erbitux™; Humira™; Raptiva™; Remicade™; ReoPro™; Prolia®; Xgeva®; Simulect™; Synagis™; Xolair™; Zenapax™; Mylotarg™; and Vectibix™. Exemplary Fc fusion proteins include fusion to soluble forms of receptors or enzymes and variants, derivatives, or analogs thereof such as, e.g., ENBREL®.

It is understood that the target protein purified using the methods described herein is one which contains an Fc region and therefore is amenable to purification by Protein A. The term "Fc region" or "Fc," as used herein, refers to those amino acid residues of an immunoglobulin molecule which interact with Protein A. The Fc region is the crystallizable tail region of an antibody and interacts with cell surface receptors called Fc receptors.

The term "Fc-binding," "binds to an Fc portion" or "binding to an Fc portion" refers to the ability of an affinity ligand described herein, to bind to the constant part (Fc) of an antibody. In some embodiments, a ligand according to the present invention binds an Fc portion of an antibody (e.g., human IgG1, IgG2 or IgG4) with an affinity of at least $10^{-7}$ M, or at least $10^{-8}$M, or at least $10^{-9}$ M.

As used herein, the term "fragment(s)" refers to a portion of a full length Fc-containing protein such as, e.g., an immunoglobulin. Examples of fragments include Fab fragments, single-chain antibody molecules, diabodies, linear antibodies, and multispecific antibodies formed from antibody fragments.

Immunoglobulins and other Fc-containing proteins which are purified using the methods described herein may be expressed using any suitable expression system or cell type. In some embodiments, an immunoglobulin or another Fc-containing protein is expressed in a mammalian cell, e.g., CHO or NS0 cells, hybridomas, mouse cells etc. In another embodiment, an immunoglobulin or another Fc-containing protein is expressed using a non-mammalian cell culture (e.g., insect cells, yeast cells, *Escherichia coli*, etc.). Following expression in a cell culture, the insoluble species are typically removed using a clarification method such as, e.g., depth filtration, centrifugation, flocculation/precipitation (e.g., acid precipitation or stimuli-responsive polymer). This clarified cell culture is typically loaded onto a Protein A column to separate the immunoglobulin or Fc-containing protein from soluble impurities such as host cell proteins. DNA, viruses, or other impurities.

As used herein, the term "purified polypeptide' or "purified protein" is an eluted product from a Protein A affinity step using the pH gradient or pH step methods as described herein. Purified polypeptides/proteins preferably contain mostly polypeptide monomers.

As used herein, the term "unpurified polypeptide," "unpurified protein," or "protein load" is a polypeptide or protein in the loading material or starting material prior to the Protein A affinity purification step.

As used herein, the term "purity of an Fc-containing protein" is defined as the monomeric species of the target protein (i.e., an Fc-containing protein) relative to the total protein eluted off of a Protein A chromatography column following a purification process, which employs a cleaning procedure described herein. Accordingly, the purity can be calculated by the ratio of total monomer to the total protein in the final elution pool. The total protein may contain one or more of protein fragments, aggregates, monomeric species of the target protein and the variants thereof.

As used herein, the term "cleaning" refers to a step during the process of purifying a target protein (e.g., an immunoglobulin or another Fc-containing protein) which entails removing trace levels of impurities left on an affinity chromatography column, e.g., a Protein A column, in order to retain the performance and integrity of the column. While the step of cleaning removes impurities from the column, it should ideally have a minimal impact on the performance of the column, as measured using binding capacity (the amount of target protein the column can purity) and/or resolution (the ability for the resin or media in the column to separate the target protein from undesirable entities). Most commercially available affinity chromatography columns, e.g., employing *Staphylococcus* Protein A or a derivative thereof) are cleaned using either an acidic solution or an alkaline solution. For example. MabSelect SuRe® Protein A column is cleaned with diluted NaOH. On the other hand, Prosep® Protein A column is generally cleaned using phosphoric acid. However, most currently commercially available Protein A resins are unstable under extremes of pH and therefore cannot be cleaned using both acidic and alkaline conditions.

As used herein, the term "cleaning-in-place" or "CIP" is a method of cleaning the interior surfaces of pipes, vessels, process equipment, filters and associated fittings, without disassembly. The benefit of using CIP is that the cleaning is faster, less labor intensive and more repeatable, and poses less of a chemical exposure risk to people. For a chromatography column, CIP refers to cleaning the resin material as well as the column body and end fittings without unpacking the column. Usually, a chromatography column cleaned after a run is immediately re-equilibrated for the next run, or sanitized for short or long term storage.

As used herein, the term "cycle" or "affinity cycle" or "Protein A affinity chromatography purification cycle" refers to a multi-step process which starts with equilibration of the chromatography column which employs a Protein A based resin, with a neutral buffer; followed by loading of a clarified cell culture feed to the column, where the clarified cell culture feed contains the Fc-containing protein to be purified (e.g., a monoclonal antibody); followed by washing the column with one to three different buffers to remove loosely bound impurities, which does not interfere with the binding of Fc-containing protein to the Protein A resin; followed by eluting the Fc-containing protein off of the Protein A column using an elution buffer (e.g., having a pH of 2.5-4.5). This multi-step process of equilibration, loading, washing and elution constitutes a cycle or a bind and elute cycle. A cycle is typically followed by a cleaning step to remove trace levels of impurities on the column before the next cycle.

As used herein, the term "campaign" refers to several rounds of individual purification processes or cycles, run one after another in order to produce a desired quantity of material within a specific time period. In case of purification of Fc-containing proteins including monoclonal antibodies, a campaign typically involves several bioreactor runs along with the subsequent purification steps in order to deliver a set quantity of the protein being purified for final fill. Although, cleaning is routinely practiced between runs within the campaign, when a campaign is complete, chromatography columns, including chromatography columns employing Protein A based ligands, are further sanitized for storage, as the columns are typically used again in the next campaign, which could be several days or weeks or months later.

As used herein, the term "sanitization" or "sanitizing" or "sanitize" is the step used after the completion of a campaign and is designed to reduce the microbial population to a level considered safe or acceptable, as determined by the FDA or other regulatory agencies. Sanitization is typically achieved using heat or chemicals. A chromatography column which is to be stored until the next campaign is generally sanitized by chemical means due to the impracticality of heat sanitization. Most affinity chromatography columns, including those employing most commercially available Protein A ligands, are sanitized using up to 0.5 M NaOH. However, 0.5 M NaOH is also known to decrease the performance of Protein A affinity chromatography resins significantly due to the deamidation effect of NaOH on the Protein A ligand. In some embodiments described herein, a solution comprising phosphoric acid, acetic acid and benzyl alcohol (PAB) is used for sanitization. Although, it has been previously shown that PAB (120 mM phosphoric acid, 167 mM acetic acid, 2.2% benzyl alcohol) may be used as a sanitant in case of the ProSep® family of Protein A affinity media, it is not considered suitable for all Protein A media, especially media that are generally cleaned or sanitized under alkaline conditions. See. M. Rogers et al., J. Chromatogr. A 1216 (2009) 4589-4596.

The term "load density" or "loading density" is the amount of the sample containing an immunoglobulin or another Fc-containing protein loaded onto a chromatography column per volume of chromatography media. The loading density is measured in g/L. In some embodiments, the sample is loaded with a loading density of 5 g/L, or 10 g/L or 12 g/L, or 15 g/L, or 20 g/L, or 30 g/L, or 40 g/L or higher.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems. Gueffroy, D., Ed. Calbiochem Corporation (1975).

The "equilibration buffer" herein is that used to prepare the solid support (with immobilized Protein A) for loading the target protein.

The "wash buffer" is used herein to refer to the buffer that is passed over the solid support (with immobilized Protein A) following loading and prior to elution of the target protein.

The term "binding capacity" refers to the amount of a molecule which will bind to a defined volume of resin or media packed in a column run under defined conditions. Binding capacity can be measured as static binding capacity or dynamic binding capacity. In case of static binding capacity, the amount of a molecule that binds to a defined volume of resin when the molecule and the resin are in contact for infinite amount of time, is determined. Static binding capacity measures the highest amount of a target molecule that a resin can bind. In practice, the value is often obtained by contacting excess of the target molecule with the resin for equal to or longer than 4 hours with minimal or no flow. Dynamic binding capacity, on the other hand, is the amount of a target molecule the resin can bind per volume of resin at a set flow rate. The dynamic binding capacity for any resin is highly dependent on the underlying conditions. In general, the lower the flow rates, the higher the dynamic binding capacity. As the flow rate approaches zero, the binding capacity approaches the maximum available capacity-static binding capacity. Without proper cleaning and sanitization, the binding capacity of a Protein A resin typically drops below the initial value after multiple bind and elute cycles. When the binding capacity is lower than a certain value which is set during a chromatography method/process development, a significant amount of the target protein could "breakthrough," or co-elute with the flow through fraction containing impurities, leading to loss of product. Proper cleaning using suitable chemicals can maintain resin binding capacity over an extended period of time. This is typically achieved using either an alkaline solution, such as 0.1 M NaOH, or an acid solution, such as 0.15 M $H_3PO_4$, based on the conditions set for the different commercially available resins. However, in case of the methods described herein, both acid and alkaline solutions can be used for cleaning, while preserving the binding capacity of the resin.

II. Protein A Chromatography

Protein A chromatography is a form of affinity chromatography, most commonly used for the purification of Fc-containing proteins such as, e.g., immunoglobulins or antibodies. Generally, a target protein (e.g., an immunoglobulin or another Fc-containing protein) is expressed in a suitable cell culture and the cell culture feed is subjected to clarification, before loading the clarified feed onto a Protein A chromatography media, e.g., packed in a chromatography column.

Protein A chromatography generally employs a solid support such as, e.g., a porous bead or a resin, having a suitable Protein A ligand immobilized thereon. The Protein A bound solid support is then packed in a chromatography column. The column may first be equilibrated with a suitable equilibration buffer. This is usually achieved by flowing 3-10 column volumes (CVs) of a neutral pH buffer, such as, phosphate saline buffer, or a Tris buffer, at pH 7-7.5, through the Protein A resin. The clarified feed containing the target protein is then contacted with the solid support in the column by loading the column with a sample containing the target protein (e.g., a clarified cell culture feed containing the target protein). The amount of clarified feed loaded is determined by the concentration of the Fc-containing protein in the feed (titer) and the binding capacity of the Fc-containing protein to the Protein A resin at a set flow rate. Typically, soluble impurities such as host cell proteins and DNA do not bind to the Protein A and hence are removed in the flow-through and diverted to the waste. After loading is complete, the column is often washed with one to three different buffers to remove loosely bound impurities, which does not interfere with the binding of the target protein to the Protein A resin. This step is also referred to as intermediate wash step. It further improves the target protein purity when it is subsequently eluted off of the Protein A column using an elution buffer (e.g., having a pH of 2.5-4.5). Common elution buffers are acetic acid and citric acid, pH 2.5-4.5. Typical flow rates for elution range from 60 column volumes (CV) per hour to 5 CV per hour. In case of gradient elution, typically elution is conducted over 5 to 60 column volumes.

In some embodiments, a high pH buffer and low pH buffer are mixed to generate a pH gradient ranging from pH 7.0 to 3.0. In some embodiments, the pH gradient starts at 7.0, or about 6.8, or about 6.6, or about 6.4, or about 6.2, or about 6.0, or about 5.8, or about 5.6, or about 5.4, or about 5.2, or about 5.0, or about 4.8, or about 4.6, or about 4.4, or about 4.2, or about 4.0, and the pH gradient ends at 3.0, or about 3.2, or about 3.4, or about 3.6, or about 3.8.

The steps of equilibration, loading, washing and elution constitute a cycle or a bind and elute cycle. This bind and elute cycle of a typical Protein A purification cycle is usually is followed by a cleaning step to remove trace levels of impurities on the column, followed by another bind and elute cycle. A typical purification campaign constitutes multiple bind and elute cycles, one after the other, with the cleaning step being performed between cycles or after each cycles.

Cleaning of Protein A affinity resin is commonly practiced after each cycle to ensure that the resin will perform purification consistently throughout the life cycle of the resin, or in other words, in order to preserve the binding capacity of the resin. Cleaning is especially important for Protein A affinity chromatography resin for two reasons: (1) Protein A resin has high initial cost compared with ion exchange or hydrophobic interaction (HIC) resins and; (2) Protein A chromatography resin is typically exposed to the clarified cell culture which contains higher level of impurities. Therefore, some residual impurities can bind to the Protein A resin, thereby leading to loss of binding capacity or increase of elution pool impurity upon re-use of the resin. This is highly undesirable in a manufacturing setting as it leads to decreased productivity (due to a decrease in binding capacity) and poorer product purity. Routine cleaning after each Protein A bind and elute cycle is, thus, critical to ensure consistent resin performance which leads to consistent product purity and process throughput.

Cleaning is typically achieved with extreme pH, e.g., using 0.15 M $H_3PO_4$ (pH 1.5) or 0.1 M NaOH (p=13), which are two commonly used cleaning reagents. For example, 0.15 M $H_3PO_4$ has been recommended and used for the ProSep® family of Protein A affinity resins. The advantage of $H_3PO_4$ cleaning is that it cleans the resin without sacrificing the binding capacity of the Protein A resin. 0.1 M NaOH, on the other hand, is recommended and used for MabSelect SuRe® family of Protein A affinity resins; however, alkaline solutions such as NaOH could potentially decrease the binding capacity of the Protein A resin over time due to deamidation of the protein ligand.

In some embodiments described herein, cleaning is performed using both acidic and alkaline solutions. In some embodiments, a chromatography column is contacted with both an acidic solution as well as an alkaline solution after each cycle. In other embodiments, a chromatography column is contacted with either an acidic solution or an alkaline solution after a cycle, such that acidic and alkaline solutions are used in an alternating manner through the purification campaign. For example, if the chromatography column is contacted with an alkaline solution after the first cycle, then it is contacted with an acidic solution after the second cycle, followed by an alkaline solution again after the third cycle and so forth. Conversely, if the chromatography column is contacted with an acidic solution after the first cycle, then it is contacted with an alkaline solution after the second cycle, followed by an acidic solution after the third cycle and so forth.

The use of acidic and alkaline solutions for cleaning results in a synergistic removal of impurities, relative to the use of just an acidic or an alkaline solution. In other words, use of both acidic and alkaline solutions for cleaning (either use of both after a cycle or use in an alternating manner as described herein), results in removal of impurities which is greater than the sum of removal with the use of just acid cleaning alone or alkaline cleaning alone through a purification process. Without wishing to be bound by theory, it is contemplated that acidic and alkaline solutions each removes a different type of impurity.

III. Exemplary Ligands Used in the Methods Described Herein

The methods according to the present invention employ Protein A ligands based on the C domain of Protein A. In some embodiments, a ligand used in the methods described herein comprises an amino acid sequence which is at least 80%, or at least 85%, or at least 90%, or at least 95%, or more identical to the amino acid sequence set forth in SEQ ID NO: 1. In some embodiments, a Protein A ligand used in the methods described herein comprises the amino acid sequence set forth in SEQ ID NO:3. In other embodiments, a Protein A ligand used in the methods described herein comprises the amino acid sequence set forth in SEQ ID NO:4. Also encompassed by the present invention are variants, fragments and derivatives of these sequences, which bind an Fc-containing protein.

IV. Exemplary Solid Supports Used in the Methods Described Herein

In some embodiments, the Protein A ligands used in the methods described herein are immobilized onto a support. e.g., a solid support or a soluble support, to generate an affinity chromatography media or resin suitable for the separation of biomolecules such as, e.g., immunoglobulins and other Fc-containing proteins.

Exemplary solid supports include those based on synthetic polymers, e.g., polyvinylether, polyvinylalcohol, polymethacrylate, polyacrylate, polystyrene, polyacrylamide, polymethacrylamide and polycarbonate.

Exemplary solid support formats include, but are not limited to, a bead (spherical or irregular), a hollow fiber, a solid fiber, a pad, a gel, a membrane, a cassette, a column, a chip, a slide, a plate or a monolith.

Any suitable technique may be used for attaching a ligand described herein to a solid support. For example, in some embodiments, the ligand may be attached to a solid support via conventional coupling techniques utilizing, e.g. amino and/or carboxy groups present in the ligand. For example, bisepoxides, epichlorohydrin. CNBr, N-hydroxysuccinimide (NHS) etc., are well-known coupling reagents. In some embodiments, a spacer is introduced between the solid support and the ligand, which improves the availability of the ligand and facilitates the chemical coupling of the ligand to the support.

In some embodiments encompassed by the present invention, more than one site on a ligand is attached to a solid support such (i.e., via multipoint attachment.

In general, attachment of a Protein A based chromatography ligands to a solid support can be achieved via many different ways, most of which are well known in the art, as well as those described herein. See. e.g., Hermanson et al., Immobilized Affinity Ligand Techniques, Academic Press, pp. 51-136 (1992).

V. Cleaning and Sanitization of Protein a Chromatography Column

Cleaning of chromatography columns is a practice that is commonly used after each cycle to maintain column performance and extend column life time. Usually, after each run is completed, a cleaning solution is loaded on to the column for 15 to 30 mins, followed by a re-equilibration buffer or a sanitization buffer (if the column is ready for storage). Common cleaning solutions are 0.05-0.3 M NaOH, or 0.15 M $H_3PO_4$. Flow rate during cleaning is typically determined based on the specific resin being used and the chromatography system. Although, NaOH is a commonly used cleaning solution in biopharmaceutical industry, acidic solution, such as, 0.15 M $H_3PO_4$, can also effectively remove contaminants and is used in certain instances.

For Protein A chromatography, it is common to use $H_3PO_4$ to clean ProSep® family of products while NaOH is used for the cleaning of MabSelect SuRe® family of products. However, most commercially available Protein A media can only be cleaned with either an alkaline solution or an acid solution.

In case of the methods described herein; however, a Protein A resin based on the C domain of *Staphylococcus aureus* immobilized onto a solid support, can be cleaned using both acid and alkaline solutions. Using both alkaline and acidic solutions results in a synergistic removal of undesired impurities as compared to each solution individually.

Sanitization of chromatography columns are commonly conducted after a column has been used in a campaign and before it is ready for storage. A sanitization solution is loaded onto the column at a preset flow rate for 3-5 column volumes. The flow is then stopped to allow a set time for the sanitant to work its way to achieve targeted microbial kill. The sanitant is then replaced with a storage buffer and the column is ready for storage. Although. NaOH is a common sanitant for ion exchange and hydrophobic interaction chromatography, it is less durable for Protein A affinity chromatography. NaOH is known to attack the asparagines on proteins which leads to degradation of proteins. It is no exception for Protein A ligand. Efforts have been made to improve alkaline stability of Protein A ligand via mutating asparagines; however, NaOH still degrades Protein A, only at a slower rate relative to wild-type. This is especially an issue for sanitization as it takes a higher concentration of NaOH (0.5 M) for a longer period of time (i.e., 3-4 hrs) compared to cleaning with NaOH (0.1-0.3 M) for 15-30 min.

A more effective sanitization solution is described herein, referred to as PAB. It consists of 120 mM phosphoric acid, 167 mM acetic acid, 2.2% benzyl alcohol. PAB kills microbes effectively and quickly. PAB has been previously described as being used with the ProSep® family of products, which can only be cleaned using an acidic solution, and was co-developed by Genentech and EMD Millipore Corporation (M. Rogers et al. J. Chromatogr. A 1216 (2009) 4589-4596).

This invention is further illustrated by the following examples which should not be construed as limiting. The contents of all references, patents and published patent applications cited throughout this application, as well as the Figures, are incorporated herein by reference.

EXAMPLES

Example 1

Generation of SpA Ligands

Synthetic genes encoding the proteins having the amino acid sequences set forth in SEQ ID NO:3 and SEQ ID) NO:4 are obtained from DNA 2.0 (Menlo Park, Calif.). The 5' end of each synthetic gene includes a codon for an initiating methionine. The 5' and 3' ends of each gene contain NdeI and BamHI restriction sites, respectively. These synthetic genes as well as the expression vector that is used, i.e., pET11a (EMD Millipore Corporation, Billerica, Mass.), are digested with NdeI and BamHI (NEW ENGLAND BIOLABS, Ipswich, Mass.), the DNA fragments are separated on a 0.7% agarose TAE gel and the appropriate DNA fragments are excised and purified using the gel extraction kit from QIAGEN (Valencia, Calif.). The purified inserts are ligated into the backbone of a pET11a or any other suitable expression vector using T4 DNA ligase (NEW ENGLAND BIOLABS, Ipswich, Mass.).

The ligation reaction is transformed into DH5α competent *E. coli* (INVITROGEN, Carlsbad, Calif.), as per manufacturer's instructions, plated on Technova LB plates containing 100 µg/mL ampicillin and incubated overnight at 37° C. In order to obtain purified DNA, individual colonies are picked and cultured overnight in LB containing 100 µg/mL ampicillin. DNA is purified using spin mini-prep kits from QIAGEN (Valencia, Calif.). The identity of recombinant plasmids is confirmed by restriction digest analysis using NdeI and BamHI (NEW ENGLAND BIOLABS, Ipswich, Mass.).

Example 2

Expression and Purification of SpA-Based Ligands

Any suitable bacterial expression system can be used for expressing the various SpA ligands described herein. For example, the protein may be expressed in an *Escherichia Coli* strain such as strain BL21 (DE3) (PROMEGA, Madison Wis.) using a pET vector such as pET11a (EMD).

A single colony is selected from a plate and grown overnight at 37° C. in LB media containing 100 µg/mL ampicillin. The overnight culture is diluted 100-fold into fresh LB media containing 100 µg/mL ampicillin and grown to a cell density such that the optical density at 600 nm is ~0.8. Following the addition of 1 mM isopropyl-beta-D-thiogalactopyranoside, cells are grown for an additional two hours. Expression is confirmed by SDS-PAGE analysis and Western blotting.

Cells are harvested by centrifugation (4000 rpm, 4° C., 5 minutes) and resuspended in 3 mL of phosphate buffered saline containing 20 mM imidazole. Cells are lysed by sonication, and cell debris is pelleted by centrifugation (4000 rpm. 4° C., 30 minutes). SpA ligands are purified using a 50 mL IgG affinity resin (Polyclonal hIgG immobilized on controlled pore glass), applying 500 mL cell lysate. Columns are washed with 30 mL phosphate buffered saline and SpA is eluted in 0.1 M citric acid, pH 3. SpA is dialyzed overnight into Milli-Q® water (EMD Millipore Corporation, Billerica, Mass.). Protein concentration is confirmed using the UV spectrometer based on theoretical extinction coefficient (Pace et. al., Protein Science 4:2411 (1995).

Example 3

Attachment of SpA-Based Ligands to a Solid Support

Subsequent to the generation and expression of various ligands, as described in Examples 1 and 2, the ligands are immobilized via multipoint attachment to a solid support.

In an exemplary experiment. Protein A ligand (amino acid sequence set forth in SEQ ID NO: 3, 10~20 mg/mL) is immobilized to crosslinked polyvinylether solid support (Merck KGaA proprietary materials) via the reaction of epoxy groups on the solid support and the numerous amino groups on the ligands in the presence of 1~1.1 M $Na_2SO_4$ overnight. (Hermanson et. al. Academic Press, 1992, page 118). The resin is designated Resin A.

Method of coupling of ligands having the amino acid sequence set forth in SEQ NO:4 and native Protein A (Lonza, Ltd., Switzerland) are similar to the process above and corresponding resins are designated Resin B and Resin C.

Example 4

Extended Exposure of Resins A, B and C to Acid and Alkaline Solutions

In this experiment, each of the Resins A, B and C described above, are exposed to various acidic and alkaline solutions. The following solutions are prepared: HCl (0.3%, v/v), pH 1.5; $H_3PO_4$ (0.15 M), pH 1.5; 0.1 M NaOH and 0.5 M NaOH.

Resins A. B, and C (2 mls of each resin is used in duplicate for each solution condition) are transferred into 5" disposable column (Evergreen Scientific, Los Angeles, Calif.) and conditioned in one of the aforementioned solutions for 5 mins. The solution is removed by vacuum and the resin is transferred to a 15 mL polypropylene conical tube (ThermoFisher, Waltham, Mass.) followed by the addition of 10 mL of the corresponding solution. The resin slurry tubes in the corresponding solution are loaded in a LabQuake® rotator (ThermoFisher, Waltham, Mass.) at room temperature for 25 hrs followed by wash in a Evergreen 5" disposable column 5 times with 4 mL of with Milli-Q® water (EMD Millipore Corporation, Billerica, Mass.) three times.

TABLE 1

Samples and test conditions. Each sample used in duplicates.

| | HCl, 0.3% v/v | $H_3PO_4$, 0.15M | 0.1M NaOH | 0.5M NaOH |
|---|---|---|---|---|
| Resin A | + | + | + | + |
| Resin B | + | + | + | + |
| Resin C | + | + | + | + |

Example 5

Static Binding Capacity Evaluation of Resins A, B, and C Before and after Extended Alkaline and Acid Exposure In this experiment, each of the Resins A, B and C (in 1 mL volume), with exposure to 0.3% HCl; 0.15 M $H_3PO_4$; 0.1 M NaOH; or 0.5 M NaOH, along with the control sample which is stored in storage buffer of 20% ethanol with 150 mM NaCl, is made into a 10% slurry in Milli-Q® water (EMD Millipore Corporation, Billerica, Mass.), 1 mL of each resin slurry is added to 15 mL of polyclonal IgG (SERACARE, 1 mg/mL)) in 10 mM phosphate saline buffer and gently mixed for 4 hours at room temperature. The reduction in UV absorbance at 280 nm is used to calculate resin IgG binding capacity before and after acid or alkaline exposure. The percentage of retained IgG binding capacity is calculated by dividing the IgG binding capacity after acid or alkaline exposure by that of the control sample which is not exposed to acid or alkaline conditions.

FIG. 1 depicts the results of such an experiment. All three resin samples demonstrate retention of more than 95% of initial binding capacity upon exposure to either 0.3% HCl or 0.15 M $H_3PO_4$ for 25 hrs relative to the control. Resins A and B retain more than 95% binding capacity upon exposure to 0.1 M NaOH relative to the control and approximately 75% of binding capacity upon exposure to 0.5 M NaOH relative to the control. Resin C retains approximately 65% binding capacity upon exposure to 0.1 M NaOH relative to the control and approximately 38% of binding capacity upon exposure to 0.5 M NaOH relative to the control. Standard deviation of the test is approximately 1-3%. Thus, the retained binding capacity upon alkaline solution exposure of Resins A and B are considered equivalent.

Example 6

Dynamic Binding Capacity Evaluation of Resin B Before and after Extended Acid Exposure In this experiment, a standard method for testing resin dynamic capacity using commercial polyclonal IgG is used. Briefly, resin B according to the present invention is packed into an Omnifit column (6.6 mm×50 mm) in 50 mM Tris w 25 mM NaCl, 5 mM ETDA, pH 7.2 (EQ buffer) and the flow rate is set at 100 cm/hr. The packed column is equilibrated with EQ buffer for 10 column volumes (CVs). Polyclonal IgG (Seracare, 2 mg/mL in EQ buffer, pH 7.2) is loaded onto the column until $UV_{280\ nm}$ reaches more than 50% of the initial IgG concentration. After washing with equilibration buffer, IgG is eluted with 0.1 M acetic acid, pH 3.0. After column equilibration using EQ buffer of the first run, the resin is washed using 0.15 M $H_3PO_4$ for 25 hrs at flow rate of 50 cm/hr, followed by another IgG dynamic capacity measurement. Another 25 hrs of exposure to 0.15 M $1H_3PO_4$ is conducted followed by a third dynamic binding capacity measurement. An exposure cycle is defined as exposure for 15 mins. Therefore, a 25 hr exposure represents a total of 100 cycles. Two 25 hr exposures represent a total of 200 cycles of exposure.

Figure 2:
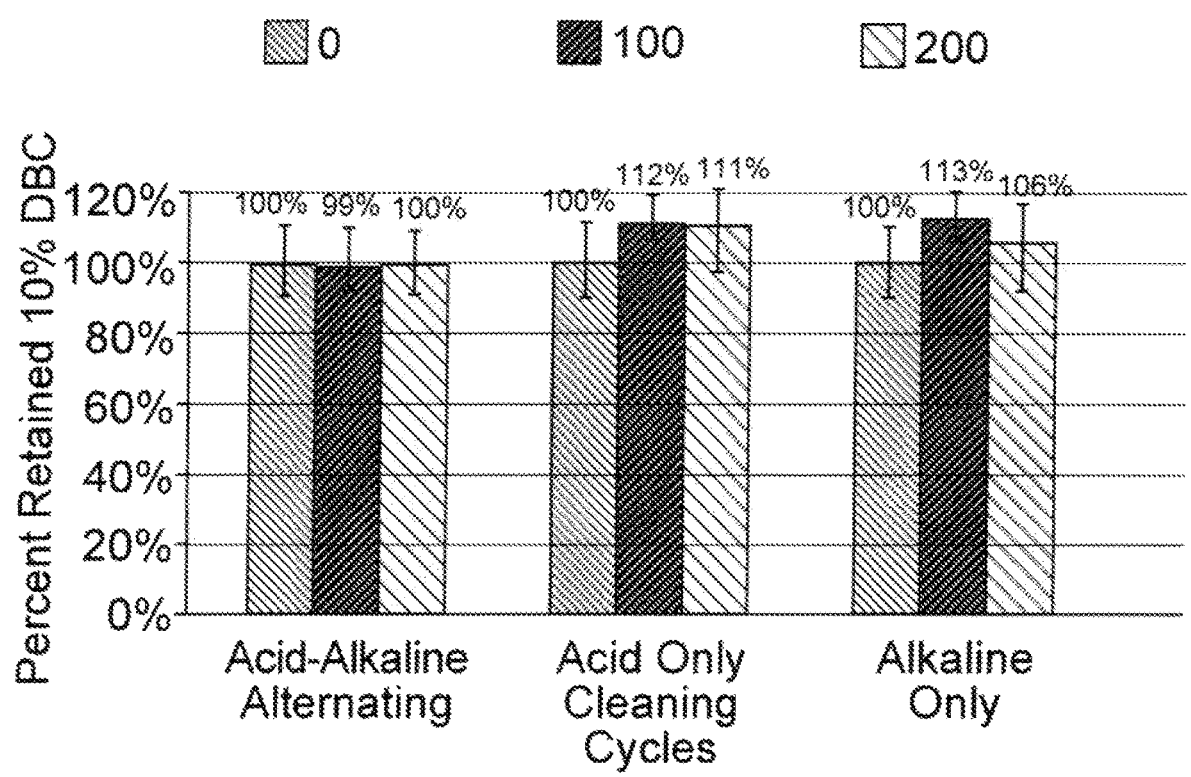
FIG. 2 is a bar graph depicting the results of an experiment to measure the percent retained dynamic binding capacity (10% at 4 min residence time) after 100 and 200 cycles of exposure of resin B to: (1) cleaning by alternating 0.1 M NaOH and 0.15 M phosphoric acid, pH 1.5, every 10 cycles; (2) cleaning with phosphoric acid cleaning only; and (3) cleaning with 0.1 M NaOH alkaline solution only. No significant change in dynamic binding capacity (10% breakthrough) is observed after 200 cycles (at 15 min/cycle) with alternating exposure of phosphoric acid and NaOH and 0.15 M $H_3PO_4$; after 200 cycles (at 15 min/cycle) exposure to 0.15 M $H_3PO_4$ only, or after 200 cycles (15 min/cycle) exposure to 0.1 M NaOH. Standard deviation is approximately 10%.

Dynamic binding capacity at 10% breakthrough is calculated based on the amount of IgG loaded when $UV_{280\ nm}$ reaches 10% of the initial IgG concentration. Measured dynamic binding capacities before and after 25 hr and 50 hr exposure are compared and shown in FIG. 2. No significant change is observed in resin dynamic binding capacity upon 200 cycles (15 min/cycle) exposure to 0.15 M $H_3PO_4$.

Example 7

Dynamic Binding Capacity Evaluation of Resin B Before and after Extended Alkaline Exposure In this experiment, a standard method for testing resin dynamic capacity using a commercial polyclonal IgG is used. Briefly, resin B according to the present invention is packed into an Omnifit column (6.6 mm×50 mm) in 50 mM Tris w 25 mM NaCl, 5 mM ETDA, pH 7.2 and the flow rate is set at 100 cm/hr. The packed column is equilibrated with EQ buffer for 10 column volumes (CVs). Polyclonal IgG (Seracare, 2 mg/mL in EQ buffer, pH 7.2) is loaded onto the column until $UV_{280\ nm}$ reaches more than 50% of the initial IgG concentration. After washing with equilibration buffer, IgG is eluted with 0.1 M acetic acid, pH 3.0. After column equilibration using EQ buffer of the first run, the resin is washed using 0.1 M NaOH for 25 hrs at flow rate of 50 cm/hr, followed by another IgG dynamic capacity measurement. Another 25 hrs of exposure to 0.1 M NaOH is conducted followed by a third dynamic binding capacity measurement. An exposure cycle is defined as 15 mins of exposure. Therefore, a 25 hr exposure represents a total of 100 cycles. Two 25 hr exposures represent a total of 200 cycles of exposure. Exposure cycle is defined as exposure for 15 mins. Thus, a 25 hr exposure represents a total of 100 cycles.

Dynamic binding capacity of 10% is calculated based on the amount of IgG loaded when $UV_{280\,nm}$ reaches 10% of the initial IgG concentration. Measured dynamic binding capacities before and after 25 hr and 50 hr exposures are compared and shown in FIG. 2. No significant change is observed in resin dynamic binding capacity upon 200 cycles (15 mins/cycle) exposure to 0.1 M NaOH.

Example 8

Dynamic Binding Capacity Evaluation of Resin B Before and after Extended Acid and Alkaline Exposure in an Alternating Manner In this experiment, a standard method for testing resin dynamic capacity using commercial polyclonal IgG is used. Briefly, resin B according to the present invention is packed into an Omnifit column (6.6 mm×50 mm) in 50 mM Tris w 25 mM NaCl, 5 mM ETDA, pH 7.2 and the flow rate is set at 100 cm/hr. The packed column is equilibrated with EQ buffer for 10 column volumes (CVs). Polyclonal IgG (Seracare, 2 mg/mL in EQ buffer, pH 7.2) is loaded onto the column until $UV_{280\,nm}$ reaches more than 50% of the initial IgG concentration. After washing with equilibration buffer, IgG is eluted with 0.1 M acetic acid, pH 3.0. After column equilibration using EQ buffer of the first run, the resin is first washed using 0.1 M NaOH for 2.5 hrs (10 cycles of 15 mins each) at a flow rate of 50 cm/hr, followed by a 30 min exposure to the neutral EQ buffer, referred to as step one. The resin is subsequently washed using 0.15 M $H_3PO_4$ for 2.5 hrs at a flow rate of 50 cm/hr, followed by a 30 min exposure to EQ buffer, referred to as step two. Steps one and two are then repeated 4 more times to reach a total acid and alkaline exposure of 25 hrs, or 100 cycles, thereby exposing the resin to acid and alkaline conditions in an alternating manner. Subsequently, another IgG dynamic capacity measurement is conducted followed by another 25 hrs of exposure to alternating 0.1 M NaOH and 0.15 M $H_3PO_4$ as described above. This is followed by yet another dynamic binding capacity measurement. Dynamic binding capacity of 10% is calculated based on the amount of IgG loaded when $UV_{280\,nm}$ reaches 10% of the initial IgG concentration. Measured dynamic binding capacities before and after 25 hr and 50 hr alternating acid and alkaline exposure are compared and shown in FIG. 2. No significant change is observed in resin dynamic binding capacity upon alternating exposure of phosphoric acid and NaOH to a total of 200 cycles (15 mins/cycle).

Example 9

Product Purity Obtained with Resin B after Extended Acid Exposure, after Extended Alkaline Exposure, and after Extended Alternating Acid and Alkaline Exposure Polyclonal IgG (Seracare, Milford, Mass.) is added to a non-expressing CHO-S feed (Xcellerex, Marlborough, Mass.) and filtered through a 0.22 um sterile filter. Final IgG concentration in the filtered feed is 3.5 mg/mL. This feed is loaded onto chromatography columns from Examples 6 (acid exposed), 7 (alkaline exposed), and 8 (acid and alkaline alternating exposed), as well as a control column packed with resin B in storage solution (20% ethanol with 150 mM NaCl), to 20 mg of IgG per mL of resin at 4 min residence time. The resin is washed with 0.1 M citrate, pH 5.5 and eluted with 0.1 M acetic acid, pH 3.0. The elution pool is analyzed for host cell protein level using Cygnus (Southport, N.C.) 3G CHO-S ELISA kit. Product purity is shown in Table 2 below.

While the host cell protein (HCP) levels of these samples are all low, the resin sample that has been cleaned with alternating acid and alkaline solutions shows the lowest level of HCP in elution pool, probably due to the synergistic cleaning effect of the acid and alkaline cleaning.

TABLE 2

| Resin, exposure | Host cell proteins (ng/mg of IgG) |
|---|---|
| Resin B control (virgin resin with no acid or alkaline exposure) | 8.4 |
| Resin B, 200 cycles acid exposure | 5.9 |
| Resin B, 200 cycles alkaline exposure | 6.9 |
| Resin B, 200 cycles acid/alkaline exposure | 3.2 |

Example 10

Retained Static Binding Capacity Study of Resins Upon Exposure to PAB Solution

Resins A and B (5 mL each, used in duplicate for each condition) are soaked in PAB solution (120 mM phosphoric acid, 167 mM acetic acid, 2.2% (v/v) benzyl alcohol) either for 4 hrs or for 24 hrs. PAB soaked resin samples are then immediately flushed with phosphate saline buffer (10 mM, pH 7.4) in 2 column volumes at least three times. Resin is then added to 1 mL volume in Milli-Q® water (EMD Millipore Corporation, Billerica, Mass.), which is then made into a 10% slurry. 1 mL of this slurry is added to 15 mL of polyclonal IgG (SERACARE, 1 mg/mL) in 10 mM phosphate saline buffer and rotated for 4 hours at room temperature. The reduction in UV absorbance at 280 nm is used to calculate capacity before and after PAB exposure. The retained IgG binding capacity is calculated by dividing the IgG binding capacity after PAB exposure at 4 hrs and 24 hrs by that of control without PAB exposure. No significant change in static binding capacity is observed after 4 hr and 24 hr exposure, as shown in Table 3.

TABLE 3

Average percent retained static binding capacity of Resins A and B upon exposure to PAB solution after 4 and 24 hr relative to control.

| | Resin A | | Resin B | |
|---|---|---|---|---|
| PAB exposure time (hr) | Average retained static binding capacity (percent) | Coefficient of variant | Average retained static binding capacity (percent) | Coefficient of variant |
| 0 | 100% | 3% | 100% | 3% |
| 4 | 102% | 2% | 102% | 2% |
| 24 | 102% | 2% | 101% | 2% |

Example 11

Resin A and B Cleaning Study with a Non-Expressing CHO Feed

Cleaning abilities of $H_3PO_4$ and NaOH for Protein A resins exposed to clarified cell culture are likely be different as $H_3PO_4$ is extremely acidic while NaOH is highly alkaline.

The difference in the cleaning ability is examined and compared based on what is left behind on a fouled Protein A resin after $H_3PO_4$ and NaOH cleaning.

A non-expressing CHO-S clarified cell culture is used to foul columns packed with resins A and B to understand the cleaning ability of an acid or an alkaline solution. Resins A and B were packed into Omnifit columns (6.6 mm i.d.x3 cm bed height) with two columns each (two columns of resin A and two columns with resin B). Flow rate of this test is set at 100 cm/hr. All four columns are equilibrated with the EQ buffer as described above and loaded/recirculated with the cell culture solution for 24 hrs. One set of columns with resins A and B are cleaned with 0.1 M NaOH for 30 min and then re-equilibrated with EQ buffer for 30 min. The other set of columns with resins A and B are cleaned with 0.15 M $H_3PO_4$, pH 1.5 for 30 min and then re-equilibrated with EQ buffer for 30 min. Resin in the top one centimeter of each column is then removed for analysis.

Example 12

Resin Extraction and Analysis of the Extractants from Example 11

Resin from top of the columns in Experiment 11 is further washed with equilibration buffer and extracted with 2% SDS in 20 mM Tris at pH 7.0 at 50° C. overnight at 250 rpm in an incubator. The next day, the samples are spun at 13500 rpm in a microcentrifuge.

SDS is then removed and exchanged to equilibration buffer using a Centricon device (3KD, EMD Millipore Corporation. Billerica. Mass.) after at least 5 buffer exchanges. A small aliquot of the buffer-exchanged resin extract is analyzed by SDS-PAGE, 2D gel, and/or LC-MS.

As observed, for resin A, acid cleaning and alkaline cleaning removes different host protein species to a different extent. This demonstrates that acid and alkaline cleaning can each remove different impurities from a fouled column. Therefore, alternating cleaning with an acidic solution, such as $H_3PO_4$, and an alkaline solution, such as NaOH results in synergistic removal of impurities and more effective cleaning effect of a Protein A column, thus, extending the life time of the column.

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

---

We claim:

1. A method of preserving the dynamic binding capacity of an affinity chromatography column over one or more affinity purification cycles, the method comprising: cleaning steps consisting essentially of cleaning the chromatography column after one or more affinity purification cycles with an acidic solution consisting essentially of phosphoric acid and having a pH lower than 3.0 wherein the affinity chromatography column comprises a Protein A media comprising a Protein A ligand derived from the C domain of *Staphylococcus aureus* Protein A immobilized onto a solid support comprising a polymer selected from the group consisting of polyvinylether, polyvinylalcohol, polymethacrylate, polyacrylate, polystyrene, polyacrylamide, polymethacrylamide and polycarbonate, wherein the dynamic binding capacity is preserved for 50-200 cycles.

2. The method of claim 1, wherein the Protein A ligand comprises an amino acid sequence selected from SEQ ID NO: 3 and SEQ ID NO: 4.

3. The method of claim 1, wherein the acidic solution comprises a pH of 2.5.

4. The method of claim 1, wherein the acidic solution comprises a pH of 2.0.

5. The method of claim 1, wherein the acidic solution comprises a pH of 1.5.

6. The method of claim 1, wherein the dynamic binding capacity is preserved for 50-100 cycles.

7. The method of claim 1, wherein the dynamic binding capacity is preserved 100-200 cycles.

8. The method of claim 1, wherein the solid support comprises a polyvinylether polymer.

9. A method of cleaning an affinity chromatography column using both acidic and alkaline solutions, the method comprising: cleaning steps consisting essentially of a) contacting the column with both acidic and alkaline solutions, wherein the acidic solution consists essentially of an acid and the alkaline solution consists essentially of an alkali, between affinity purification cycles; or b) contacting the column with either an acidic solution after a cycle or an alkaline solution after a cycle, wherein the acidic solution consists essentially of an acid and the alkaline solution consists essentially of an alkali, such that the acidic and alkaline solutions are used in an alternating manner, wherein the affinity chromatography column comprises a Protein A media comprising a Protein A ligand derived from the C domain of *Staphylococcus aureus* Protein A immobilized onto a solid support, wherein the dynamic binding capacity is preserved for 50-200 cycles.

10. The method of claim 9, wherein the solid support comprises a polymer selected from the group consisting of polyvinylether, polyvinylalcohol, polymethacrylate, polyacrylate, polystyrene, polyacrylamide, polymethacrylamide and polycarbonate.

11. The method of claim 9, wherein the acidic solution consists essentially of phosphoric acid.

12. The method of claim 9, wherein the alkaline solution consists essentially of sodium hydroxide.

13. The method of claim 9, wherein the method results in a synergistic removal of impurities.

14. The method of claim 9, wherein the ligand comprises an amino acid sequence selected from SEQ ID NO:3 or SEQ ID NO:4.

15. The method of claim 1, wherein the alkaline solution is from 0.1 M sodium hydroxide to 0.5 M sodium hydroxide.

16. The method of claim 9, wherein the sodium hydroxide solution is from 0.1 M sodium hydroxide to 0.5 M sodium hydroxide.

17. The method of claim 9, wherein the dynamic binding capacity is preserved 50-100 cycles.

18. The meth od of claim 9, wherein the dynamic binding capacity is preserved 100-200 cycles.

19. The method of claim 1, wherein there is no significant change in dynamic binding capacity for 50-200 cycles.

20. The method of claim 9, wherein there is no significant change in dynamic binding capacity for 50-200 cycles.

* * * * *